United States Patent [19]
Uno et al.

[11] Patent Number: 5,766,864
[45] Date of Patent: Jun. 16, 1998

[54] METHOD OF MEASURING INTERFERON ACITIVITY

[75] Inventors: Kazuko Uno, Takatuki; Tsunataro Kishida, Kyoto; Keiji Fujioka, Toyonaka, all of Japan; Yoshihiro Takada, Irvington, N.Y.; Takayuki Sato, Osaka, Japan

[73] Assignee: Sumitomo Pharmaceuticals Company, Ltd., Osaka-fu, Japan

[21] Appl. No.: 551,613

[22] Filed: Nov. 1, 1995

[30] Foreign Application Priority Data

Nov. 1, 1994 [JP] Japan .................... 6-293724

[51] Int. Cl.$^6$ .................... C12Q 1/25; C12N 5/08
[52] U.S. Cl. .................... 435/7.21; 435/366
[58] Field of Search .................... 435/29, 7.72, 7.21, 435/366

[56] References Cited

FOREIGN PATENT DOCUMENTS

| 0217102 | 4/1987 | European Pat. Off. . |
|---|---|---|
| 0254593 | 1/1988 | European Pat. Off. . |
| 2505845 | 11/1982 | France . |
| 3816534 | 11/1989 | Germany . |
| 2048472 | 12/1980 | United Kingdom . |

OTHER PUBLICATIONS

R. Lleonart et al., *Bio/Technology*, vol. 8, pp. 1263–1267, Dec. 1990.

*Primary Examiner*—Gary L. Kunz
*Attorney, Agent, or Firm*—Birch, Stewart, Kolasch & Birch, LLP

[57] ABSTRACT

A method of measuring the activity of interferon-$\alpha$, $\beta$ or $\omega$, which comprises bringing a sample containing interferon into contact with a cell and determining an induced protein is provided.

2 Claims, 8 Drawing Sheets

METHOD OF MEASURING INTERFERON ACITIVITY

FIELD OF THE INVENTION

The present invention relates to a method of measuring the biological activity of interferon-α, interferon-β or interferon-ω, specifically, to a method of measuring the biological activity of interferon-α, β or ω, which comprises bringing a sample containing interferon into contact with a cell and determining a protein(s) induced thereby.

BACKGROUND OF THE INVENTION

Interferon is a protein which was originally discovered as a virus-inhibiting factor by Isaacs and Lindemann (A. Isaacs and J. Lindenmann, Proc. Roy. Soc. Ser. B., 147: 258, 1957) and is currently classified into four groups, i.e., interferon-α, β, γ and ω. These interferons are known to exert, in addition to antiviral activity, various activities such as antitumor activity through cell growth suppression, the enhancement of expression of cell surface antigens and the like and to participate into the immune system response through the stimulation of macrophage phagocytic ability and enhancement of natural killer activity and the like.

Owing to these various activities, interferon has been expected to be useful as antiviral and antitumor drugs and is currently used widely as a medicament for treating hepatitis B and C, acute myelocytic leukemia, multiple myeloma, malignant melanoma and the like. It has long been known that interferon is responsible for symptoms of various diseases such as type I diabetes, and recently been shown that the amount of interferon produced in blood cells could provide important information in the evaluation of such symptoms (M. Kita et al., J. Clin. Lab. Anal., 5: 238–241, 1991; and S. Nakagawa et al., Japanese Journal of Urology, 81: 262–267, 1990).

These facts indicate that the determination of interferon activity is essential to promote the clinical application thereof or to grasp a given symptom adequately. Actually, interferon activity is often determined for various purposes.

Because of complexity, the mechanism of action of interferons has been elucidated only partially so far. However, it has recently turned out that interferons stimulate the production of proteins such as 2'→5' oligoadenylate synthetase, phosphodiesterase and the like, thereby exerting the antiviral action. Based on this relationship, interferon activity has been confirmed by measuring 2'→5' oligoadenylate synthetase produced in human and animals following the administration of interferon.

However, it has never been reported that there is a relationship between the activity of interferon added and the amount of 2'→5' oligoadenylate synthetase induced thereby, that is, the interferon activity can be determined through the measurement of the amount of 2'→5' oligoadenylate synthetase.

As for the method of measuring the activity of interferon-α, β or ω, there have been widely known biological or immunological methods.

In the biological methods, a sample containing interferon is brought into contact with a cell highly sensitive to interferon such as FL cell, WISH cell and the like which is followed by addition of a given amount of a virus infectious to the cell such as Sindbis virus, Vesicular stomatitis virus (VSV) and the like. The interferon activity is determined through the measurement of the ability of a cell to resist to virus, which ability has been induced by interferon. Accordingly, this is an indirect method as principle. The activity of cells in resisting to virus is determined using as an indication the suppression of the growth of virus by measuring the number of viral plaques or the amount of synthesized viral nucleic acids or by determining directly the yield of virus. The interferon titer is evaluated from the dilution ratio of a sample solution which suppresses 50% growth of virus. In the biological method, the cytopathic effect (CPE), i.e., the destruction effect resulting from the growth of viruses in a cell is also used as an indication of interferon activity. The interferon titer is evaluated from the dilution ratio of a sample solution capable of inhibiting 50% of CPE in cells. The interferon titer based on the international standard unit (IU) can be obtained by calibrating the measurements with those obtained using interferon standard in the same manner. (S. Kobayashi et al., "Meneki Seikagaku Jikkenho (Zoku Seikagaku Jikken Koza 5)", Japanese Biochemical Soc. ed., pp. 2–45, Tokyo Kagaku Dojin, Tokyo, 1986). At present, a biological method using CPE as an indication is most widely employed.

According to the biological methods above, the amount of biologically active interferons (the interferon activity) can be determined because they are based on the antiviral activity of cells resulted from the binding between interferon-α, β or ω and receptors therefor on cell surface. These methods, however, involve complicated procedures and are not sensitive enough in detection. Although the detection limit varies depending on assay system, it could be theoretically estimated to be about 6 IU/ml when using CPE as an indication (S. Yamazaki, Pharma Medica, 4 (9): 111–118, 1986).

On the other hand, immunological methods employ anti-interferon antibodies and can be classified into radioimmunoassay and enzyme immunoassay based on the determining means, and into competitive and non-competitive assays based on the manner of combination of antibodies. For example, a non-competitive enzyme immunoassay can be carried out by allowing interferon and enzyme-labeled anti-interferon antibodies to bind to anti-interferon antibodies immobilized on a solid phase successively in this order, and detecting the bound interferon by means of enzyme reaction (H. Ishiko et al., Journal of Clinical and Experimental Medicine, 192 (3): 182, 1984). Alternatively, it can be carried out by using anti-interferon antibody instead of enzyme-labeled anti-interferon antibody in the method above, followed by allowing an enzyme-labeled anti-antibody antibodies to bind to the solid phase (Ora Horovitz et al., Immunoenzymatic Techniques, S. Auramens et al. ed., pp. 193, Elsevier Science Publishers B.V., 1983).

The detection limit of interferon specifically bound to anti-interferon antibody in the immunological methods above is also estimated to be about 2 IU/ml (Biosource International Company, Human Interferon-α ELISA kit), and therefore biological and immunological methods give the detection of interferon to the same extent. However, the immunological methods are not suited for determination of interferon activity because both of biologically-active and inactive interferons are detected. Therefore, a method by which biological activity of interferon can be readily detected with higher sensitivity has been desired.

SUMARY OF THE INVENTION

Thus, one of purposes of the present invention is to provide a method of measuring the biological activity of interferon more simply and sensitively than conventional methods.

The present inventors have investigated intimately to develop a method of measuring a biological activity of interferon of a slight amount and found that there is a relationship between the amount of a protein induced by interferon and the activity thereof. This finding led the present inventors to establish the method of measuring the interferon activity in a sample through the determination of a protein induced thereby in cells.

Accordingly, the present invention provides a method of measuring the activity of interferon-α, β or ω, of which gist is as follows.

(1) A method of measuring the activity of interferon-α, β or ω, which comprises bringing a sample containing interferon into contact with a cell and determining a protein induced.

(2) The method as described in (1) above wherein the protein is an enzyme.

(3) The method as described in (2) above wherein the enzyme is 2'→5' oligoadenylate synthetase or phosphodiesterase.

(4) The method as described in any one of (1) to (3) above wherein the cell is selected from the group consisting of leukocyte, monocyte, lymphocyte, fibroblast and epithelial cells.

(5) The method as described in any one of (1) to (3) above wherein the cell is an established cell line of a cell selected from the group consisting of monocyte, lymphocyte, fibroblast and epithelial cells.

(6) The method as described in (4) above wherein the cell is human cell.

(7) The method as described in (5) above wherein the cell is an established human cell line.

(8) The method as described in (7) above wherein the established cell line is selected from the group consisting of THP-1, U-937, H9, FL and WISH cells.

Figure 1:
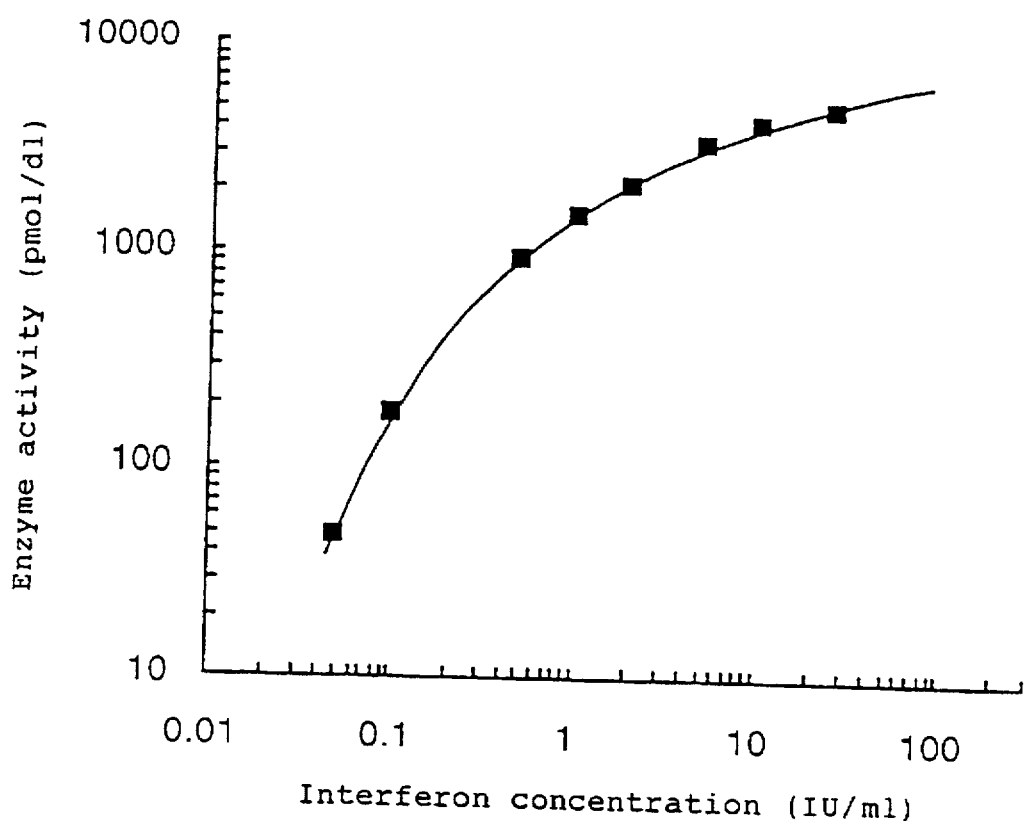
FIG. 1 is a graph showing the relationship between the concentration of interferon-α and the activity of 2'→5' oligoadenylate synthetase which induced by bringing 10% fetal bovine serum-containing Eagle's minimum essential medium (Nissui Pharmaceutical Co., Ltd.), each containing interferon-α of different and known activity into contact with THP-1 cells (see, Example 1 below).

One of the characteristics of the present invention is that a sample to be tested is brought into contact with a cell; a protein induced by an interferon in the sample is determined; and the activity of the interferon (i.e., interferon-α, β or ω) in the sample is evaluated on the basis of calibration curve showing the relationship between the protein produced in a cell and the activity of standard interferon-α, β or ω. The present invention will be hereinafter described in more detail.

As for interferon to be determined by the present method, there is no limitation as far as it is originated from mammals including human, monkey, cattle, cat, dog, rabbit, rat, mouse and the like.

As for type of interferon, there is no limitation on condition that it binds to interferon receptor type I (see, Journal of Clinical Therapeutics & Medicines, 19 (6): 1540–1544 (1993); and Biomedicine & Therapeutics, 27 (10): 1159–1163 (1993)). Specific examples include interferons-α, β and ω. Further, the present method is not restricted to any source of interferon and applicable to a sample derived from natural materials (e.g., leukocyte, fibroblast, lymphocyte and the like), that derived from natural materials (e.g., cell line), or that prepared by recombinant DNA technology. As mentioned above, the present method is applicable to an interferon of any type provided that it binds to interferon receptor type I, including a variant which has one or more changes in the amino acid sequence due to amino acid substitution, deletion or insertion while retaining the binding activity.

Any cells can be used in the present method as far as they are sensitive to a given interferon to be measured. Thus, any cells capable of being induced to produce a given protein when an interferon binds to cell surface receptors in such a manner that the amount of said protein relates to the activity of the interferon and is determined depending on said activity. Specific examples of cells usable in the present method include leukocyte, monocyte, lymphocyte, fibroblast and epithelial cell of species producing an intended interferon to be measured; and established cell lines from various cells such as monocyte, lymphocyte, fibroblast, epithelial cell and the like. Among them, the established cell lines of monocyte, lymphocyte, fibroblast, epithelial cell and the like are preferred.

For example, when human interferon-α is to be measured, a human cell such as human leukocyte, monocyte, lymphocyte, fibroblast, epithelial cell or the like, or an establish cell line from human monocyte, lymphocyte, fibroblast, epithelial cell or the like can be used. The established cell lines are preferred. Examples of such cell lines include THP-1 cell (human monocyte-originated cell line; available from Japan Cancer Research Resource Bank (JCRB) in National Institute of Health Sciences in Japan); U-937 cell (histiocytic lymphoma-originated cell line, available from JCRB); H9 cell (lymphocyte-originated cell line, available from Fujisaki Cell Center, Hayashibara Biochemical Laboratories Inc.); FL cell (available from Dainippon Pharmaceutical Co., Ltd.) and WISH cell (amnion-originated cell line). THP-1 or U-937 cell is especially preferred. When an interferon of animals other than human is to be measured, any cells suited should be selected. For example, measurement of an interferon of mouse, rabbit, monkey or cattle, L929 cell (mouse), RK-13 cell (rabbit), Vero cell (monkey) or MDBK cell (cattle) can be used, respectively. Any necessary cell line can be obtained from commercial or non-commercial sources including a cell bank of an institute such as National Institute of Health Sciences, a trader such as Dainippon Pharmaceutical Co., Ltd. and the like.

In the present method, any proteins which are inducible when interferon-α, β or ω binds to interferon receptor type I without depending on gene manipulation can be used. Example of such protein is an enzyme, specifically, 2'→5' oligoadenylate synthetase or phosphodiesterase.

The determination of thus induced protein can be carried out by any of known methods, for example, immunochemical method, quantitative assay method by means of liquid chromatography, an enzyme activity measuring method wherein the product of enzyme reaction is determined directly. Commercially available kits for measurement can be also used in the determination of proteins. The data obtained by measurement may represent absolute value, amount of protein or enzyme activity.

The measurement of interferon activity according to the present method can be carried out, for example, in the following manner.

Firstly, appropriate number of cells selected to be used are placed in each vessel. The cells may have been previously suspended in a suitable medium or buffer solution. Examples of medium and buffer include RPMI1640 and Eagle's minimum essential medium containing suitable amount of fetal bovine serum, and phosphate buffer, respectively. Vessels usable in the present method are a test tube with a cap, cell culture dish, microplate, 96- well cell culture plate and the like, but should not be limited thereto. The number of cells to be added can be, for example, between $5 \times 10$ to $1 \times 10^3$ $1 \times 10^6$/vessel, preferably $1 \times 10^4$ to $5 \times 10^5$/vessel, but should not be limited thereto.

Secondary, a sample to be tested is added to the vessel containing cells. In another vessel, an authentic sample containing interferon standard is added. Any samples which may contain interferon including, for example, serum, plasma, buffer solution, medium, supernatant of cell culture and the like can be used on condition that the sample is free from cytotoxic components. Specifically, the sample can be Eagle's minimum essential medium (with or without 10% fetal bovine serum); human serum or plasma; serum, plasma and organ homogenate of animals such as rabbit, rat and the like; supernatant of cell culture of Namalwa cell and the like; phosphate buffer; Tris-glycine buffer and the like. When the concentration of interferon in a sample is assumed to be high, it is preferred to dilute the sample with serum or the like which does not contain interferon before adding to the vessel for measurement.

After the sample is added, the cells are incubated for a certain period of time so that interferon in sample acts on cells. There is no limitation as to the incubation time on condition that it is sufficient for interferon to exerts its action. Specifically, it may be about 3 to 48 hours, preferably about 6 to 24 hours, and more preferably about 12 to 24 hours. The incubation temperature may be the same as that generally used in incubation of the selected cell. After incubation, the cells are subjected to cell breakage so as to facilitate the defemination of induced protein. The cell breakage can be carried out by any of known methods such as ultrasonic treatment, freezing and thawing method, osmotic pressure treatment or mechanical breakage, or by increasing the penetrating property of cell membrane with organic solvents, surfactants and the like.

Then, the protein is determined. The determination can be conducted using known methods. For example, when the protein is 2'→5' oligoadenylate synthetase, 2-5A kit "EIKEN" (manufactured by Eiken Chemical Co., Ltd.) can be used. When the protein is phosphodiesterase, the method of Russel et al. (J. Biol. Chem., 248: 1334, 1973) can be used. In the determination of protein, the mixture containing disrupted cells can be used after purification so as to remove contaminants or as it is if it does not contain any substances affecting the determination.

Finally, the activity of interferon-α, β or ω in the sample is evaluated from the amount of the protein on the basis of a calibration curve showing the relationship between the amount of protein and the activity of interferon-α, β or ω, which was induced by allowing interferon-α, β or ω of different and known activity to act on cells.

As will be hereinafter described, it is now possible to measure the biological activity of interferon in a sample more conveniently and sensitively according to the method of the present invention.

The following Examples are provided to further describe the present invention but should not be construed as limiting the scope of the present invention.

In the Examples below, the following materials are used.

Interferon-α : Sendai virus-induced human lymphoblast interferon-α, Sumitomo Pharmaceutical Co., Ltd;

Interferon-β : natural type interferon-β from human fibroblast cell, Toray Industries Co., Ltd.

RPMI1640 medium : Nissui Pharmaceutical Co., Ltd.

THP-1 cell: human monocyte-originated cell line, Japan Cancer Research Resource Bank (JCRB) in National Institute of Health Sciences, Japan.

U-937 cell: histiocytic lymphoma-originated cell line, JCRB.

H9 cell: lymphocyte-originated cell line, Fujisaki Cell Center, Hayashibara Biochemical Laboratories Inc.

FL cell: Dainippon Pharmaceutical Co., Ltd.

In the Examples below, the number of cells used was determined by counting living cells after staining with trypan blue.

EXAMPLE 1

Two hundred microliters each of 10% fetal bovine serum-containing Eagle's minimum essential medium (Nissui Pharmaceutical Co., Ltd.), each containing interferon-α of different and known activity, were placed in a tube equipped with a circular cap (Falcon 2083, hereinafter, referred to as "tube") separately as a sample. To the tube was added THP-1 cells ($1.6 \times 10^5$) suspended in 200 µl of RPMI1640 medium. After incubating for 20 hr at 37° C. under 5% $CO_2$ gas-phase, the cells were disrupted by freezing and thawing method. The activity of 2'→5' oligoadenylate synthetase in the resulting solution was determined using 2-5A kit "EIKEN" (Eiken Chemical Co., Ltd.) according to the manufacturer's instructions. As a control, Eagle's minimum essential medium free from interferon-α was treated in the same manner to obtain a blank value. The value obtained by subtracting the blank value from each measurement was plotted as enzyme activity in a graph (FIG. 1). In FIG. 1, the ordinate shows the enzyme activity and the abscissa the concentration of interferon-α.

FIG. 1 shows that there is a constant relationship between the concentration of interferon-α and the activity of 2'→5' oligoadenylate synthetase and that the said relationship is reproducible. This means that it is possible to evaluate the activity of interferon-α, through the determination of the activity of 2'→5' oligoadenylate synthetase. FIG. 1 shows that the detection limit of the method of measuring the interferon activity of the present invention ranges from about 0.05 to 0.1 IU/ml and that the sensitivity thereof is about 60 to 120 times that of the conventional biological method which uses as an indication the degree of resistance against virus and whose detection limit is about 6 IU/ml.

EXAMPLE 2

Figure 2:
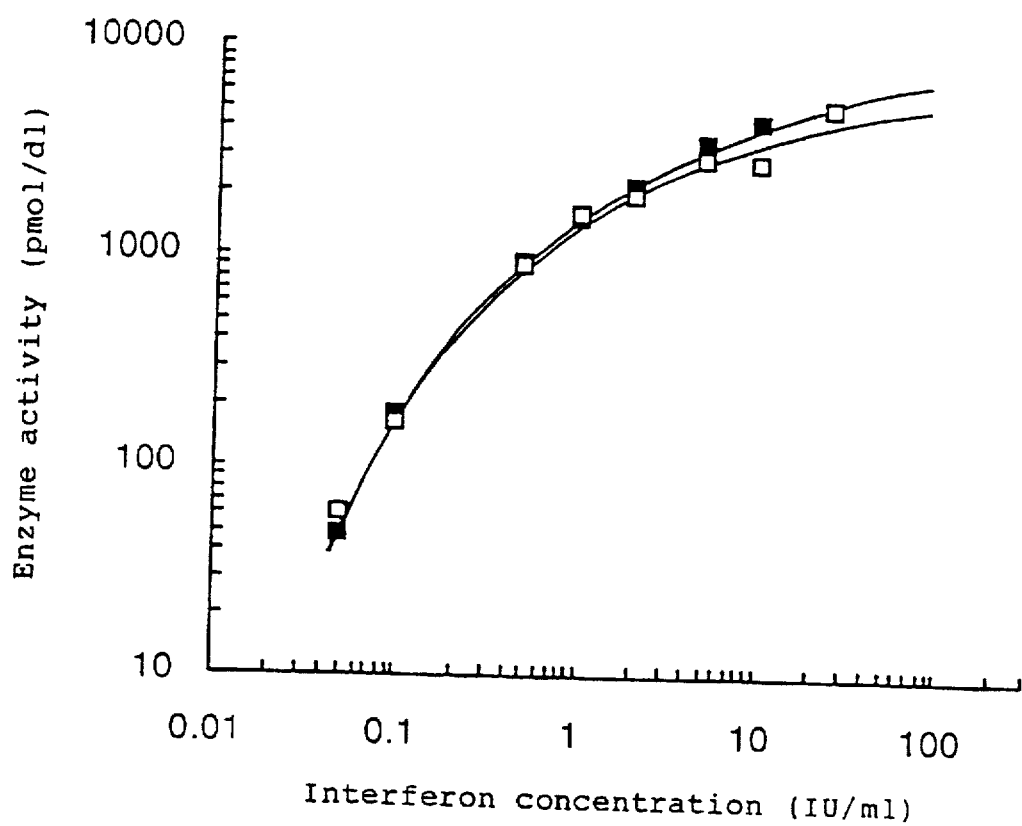
FIG. 2 is a graph showing the relationship between the concentration of interferon-α and the activity of 2'→5' oligoadenylate synthetase which is induced by bringing 10% fetal bovine serum-containing Eagle's minimum essential medium (■, see, Example 1 below) and human serum (═, see, Example 2 below), each containing interferon-α of different and known activity into contact with THP-1 cells.

Two hundred microliters each of human serum, each containing interferon-α of different and known activity, were placed in a tube separately as a sample. To the tube was added a suspension of THP-1 cells ($1.6 \times 10$) in 200 µl of RPMI1640 medium. After incubating for 20 hr at 37° C. under 5% $CO_2$ gas-phase, the cells were disrupted by freezing and thawing method. The activity of 2'→5' oligoadenylate synthetase in the resulting solution was determined in a manner similar to that of Example 1. The value obtained by subtracting the blank value from each measurement was plotted as enzyme activity in a graph (□, FIG. 2). The results obtained in Example 1 are also shown in FIG. 2 (■). In FIG. 2, the ordinate shows the enzyme activity and the abscissa the concentration of interferon-α.

FIG. 2 shows that there is a constant relationship between the concentration of interferon-α and the activity of 2'→5' oligoadenylate synthetase and that the said relationship is reproducible in the case of human serum sample too. This means that it is possible to measure the activity of interferon-α in not only Eeagle's minimum essential medium but also in serum samples according to the present method.

EXAMPLE 3

One hundred and fifty microliters each of 10% fetal bovine serum-containing Eagle's minimum essential medium, each containing interferon-β of different and known activity, were placed in a 96-well cell culture plate separately as a sample. To the plate was added THP-1 cell ($4.5 \times 10^4$) suspended in 150 µl of RPMI1640 medium. After incubating for 20 hr at 37° C. under 5% $CO_2$ gas-phase, the cells were disrupted by freezing and thawing method. The activity of 2'→5' oligoadenylate synthetase in the resulting solution was determined in a manner similar to that of Example 1. The value obtained by subtracting the blank value from each measurement was plotted as enzyme activity in FIG. 3, wherein the ordinate shows the values of enzyme activity and the abscissa the concentration of interferon-β.

Figure 3:
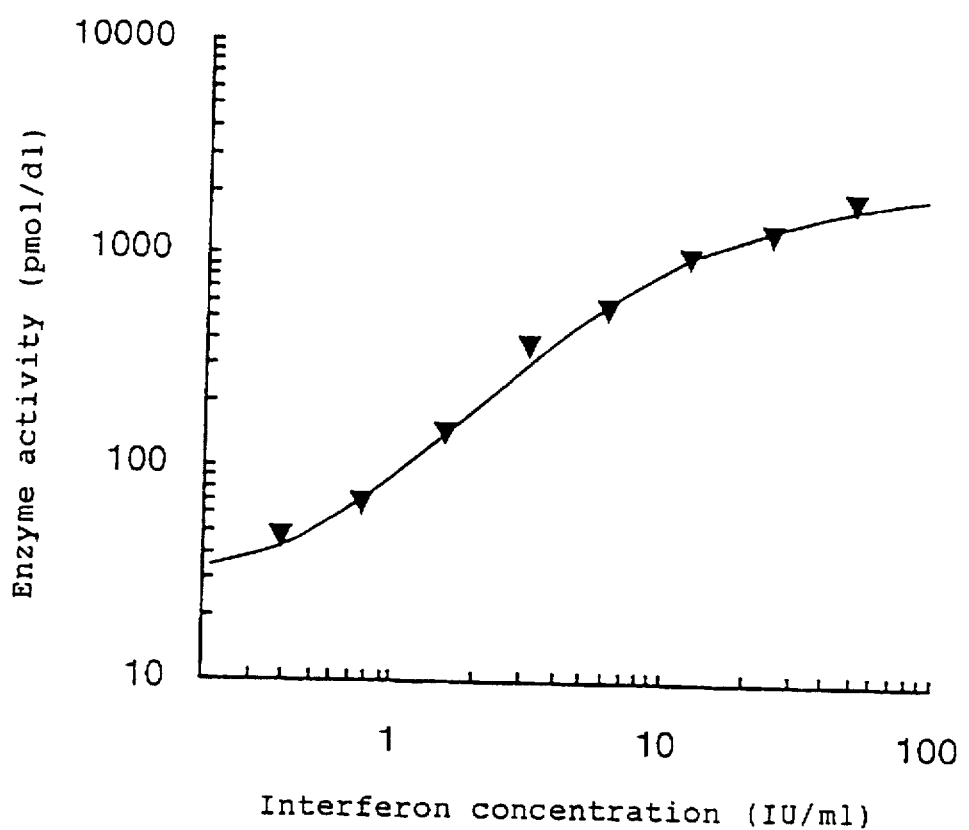
FIG. 3 is a graph showing the relationship between the concentration of interferon-β and the activity of 2'→5'oligoadenylate synthetase which is induced by bringing 10% fetal bovine serum-containing Eagle's minimum essential medium, each containing interferon-β of different and known activity into contact with THP-1 cells (see, Example 3 below).

FIG. 3 shows that there is a constant relationship between the concentration of interferon-β and the activity of 2'→5' oligoadenylate synthetase and that the said relationship is reproducible. This means that the present method is also applicable to the measurement of activity of interferon-β.

EXAMPLE 4

Two hundred microliters each of 10% fetal bovine serum-containing Eagle's minimum essential medium, each containing interferon-α of different and known activity, or 200 µl each of human serum, each containing interferon-α of different and known activity, were placed in a tube separately as a sample. To the tube was added a suspension of U-937 cell ($1.6 \times 10^5$) suspended in 200 µl of RPMI1640 medium. After incubating for 20 hr at 37° C. under 5% $CO_2$ gas-phase, the cells were disrupted by freezing and thawing method. The activity of 2'→5' oligoadenylate synthetase in the resulting solution was determined in a manner similar to that of Example 1. The value obtained by subtracting the blank value from each measurement was plotted as enzyme activity in FIG. 4, wherein ▲ represents the results from samples in 10% fetal bovine serum-containing Eagle's minimum essential medium and Δ those from samples in human serum, and the ordinate shows the enzyme activity and the abscissa the concentration of interferon-α.

Figure 4:
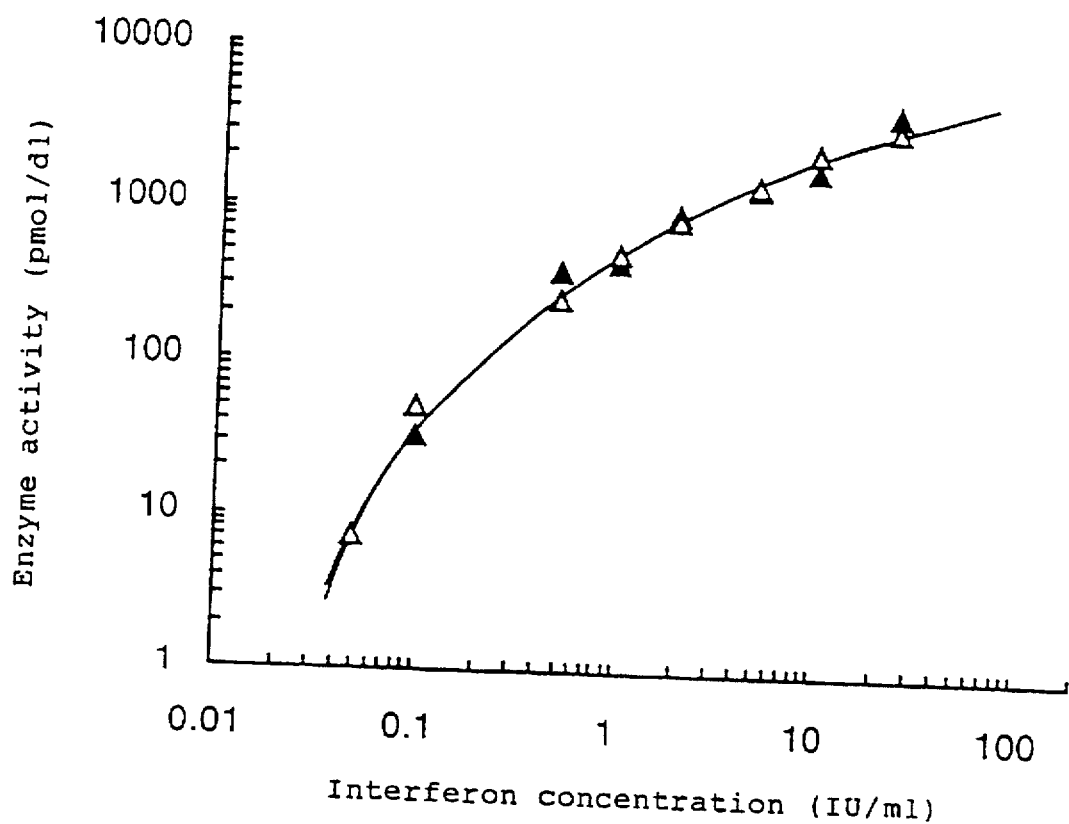
FIG. 4 is a graph showing the relationship between the concentration of interferon-α and the activity of 2'→5' oligoadenylate synthetase which induced by bringing 10% fetal bovine serum-containing Eagle's minimum essential medium, each containing interferon-α of different and known activity (▲), and human serum each containing interferon-α of known different activity (△), respectively (see, Example 4 below), into contact with U-937 cells.

FIG. 4 shows that there is a relationship between the concentration of interferon-α and the activity of 2'→5' oligoadenylate synthetase and that the same result can be obtained using human serum sample too. This means that it is possible to measure the activity of interferon-α in a sample in serum as well as in assay medium using U-937 cell too.

EXAMPLE 5

To 200 µl each of 10% fetal bovine serum-containing Eagle's minimum essential medium, each containing interferon-α of different and known activity, was added H9 cell ($1.6 \times 10^5$) suspended in 200 µl of RPMI1640 medium. After incubating for 20 hr at 37° C. under 5% $Co_2$ gas-phase, the cells were disrupted by freezing and thawing method. The activity of 2'→5' oligoadenylate synthetase in the resulting solution was determined in a manner similar to that of Example 1. The value obtained by subtracting the blank value from each measurement was plotted as enzyme activity in FIG. 5, wherein the ordinate shows the enzyme activity and the abscissa the concentration of interferon-α.

Figure 5:
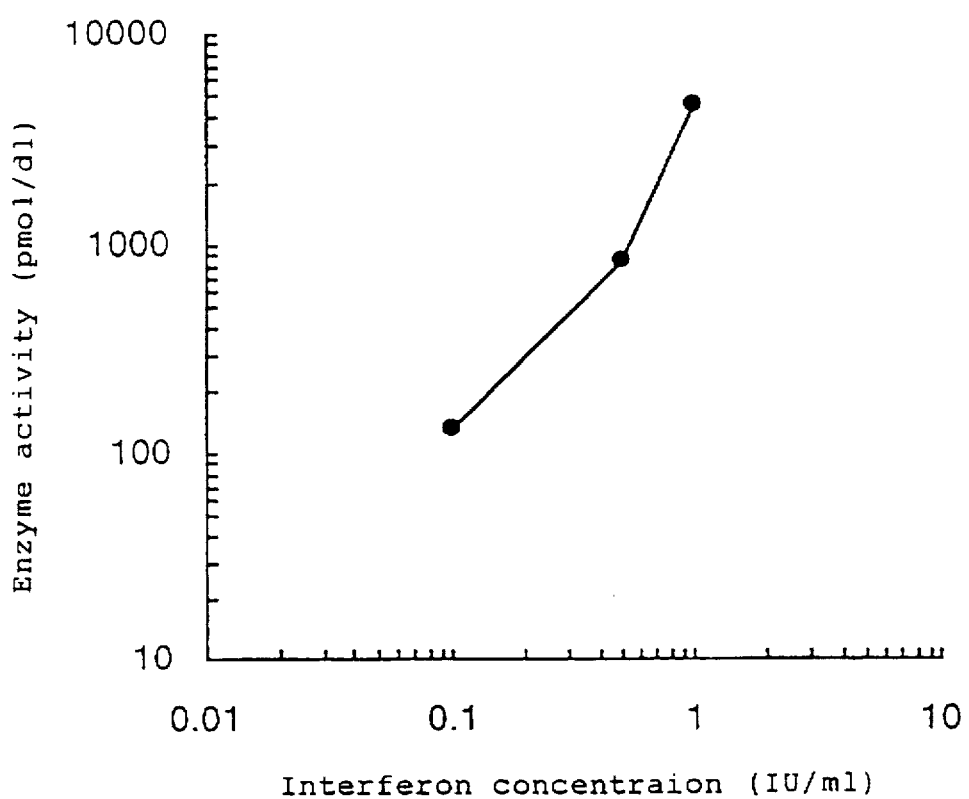
FIG. 5 is a graph showing the relationship between the concentration of interferon-α and the activity of 2'→5' oligoadenylate synthetase which is induced by bringing 10% fetal bovine serum-containing Eagle's minimum essential medium, each containing interferon-α of different and known activity into contact with H9 cells (see, Example 5 below).

FIG. 5 shows that there is a constant relationship between the concentration of interferon-α and the activity of 2'→5' oligoadenylate synthetase. This means that it is possible to measure the activity of interferon-α using H9 cells too.

EXAMPLE 6

One hundred fifty microliters each of 10% fetal bovine serum-containing Eagle's minimum essential medium, each containing interferon-α of different and known activity, or 150 µl each of 10% fetal bovine serum-containing Eagle's minimum essential medium, each containing interferon-β of different and known activity, were placed in a 96-well cell culture plate separately as a sample. To the plate was added FL cell ($4.5 \times 10^4$) suspended in 150 µl of 10% fetal bovine serum-containing Eagle's minimum essential medium. After incubating for 20 hr at 37° C. under 5% $CO_2$ gas-phase, the cells were disrupted by freezing and thawing method. The activity of 2'→5' oligoadenylate synthetase in the resulting solution was determined in a manner similar to that of Example 1. The value obtained by subtracting the blank value for each sample from the corresponding measurement was plotted as enzyme activity in FIG. 6, wherein ♦ represents the results from the samples containing interferon-α and Δ those from he samples containing interferon-β, and the ordinate shows the enzyme activity and the abscissa the concentration of interferon-α and -β.

Figure 6:
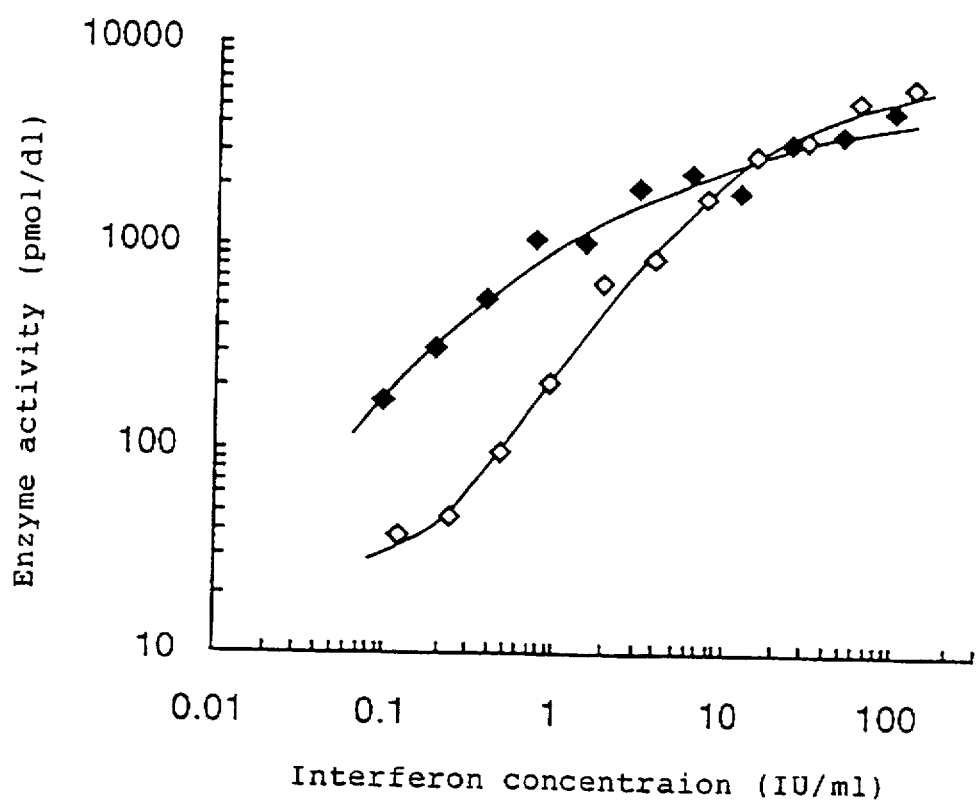
FIG. 6 is a graph showing the relationship between the concentration of interferon and the activity of 2'→5' oligoadenylate synthetase which induced by bringing 10% fetal bovine serum-containing Eagle's minimum essential medium, each containing interferon-αof different and known activity (♦) and 10% fetal bovine serum-containing Eagle's minimum essential medium, each containing interferon-β of different and known activity (◊), respectively (see, Example 6 below), in contact with FL cells.

FIG. 6 shows that there is a relationship between the concentration of interferon-α and β and the activity of 2'→5' oligoadenylate synthetase. This means that it is possible to measure the activity of both of interferon-α and β using FL cell too.

EXAMPLE 7

To 200 μl each of 10% fetal bovine serum-containing Eagle's minimum essential medium, each containing interferon-α of different and known activity, was added human monocyte ($1.6 \times 10^5$, separated from blood of healthy human by elutriation method) suspended in 200 μl of RPMI1640 medium. After incubating for 20 hr at 37° C. under 5% $Co_2$ gas-phase, the cells were disrupted by freezing and thawing method. The activity of 2'→5' oligoadenylate synthetase in the resulting solution was determined in a manner similar to that of Example 1. The value obtained by subtracting the blank value from each measurement was plotted as enzyme activity in FIG. 7, wherein the ordinate shows the enzyme activity and the abscissa the concentration of interferon-α.

Figure 7:
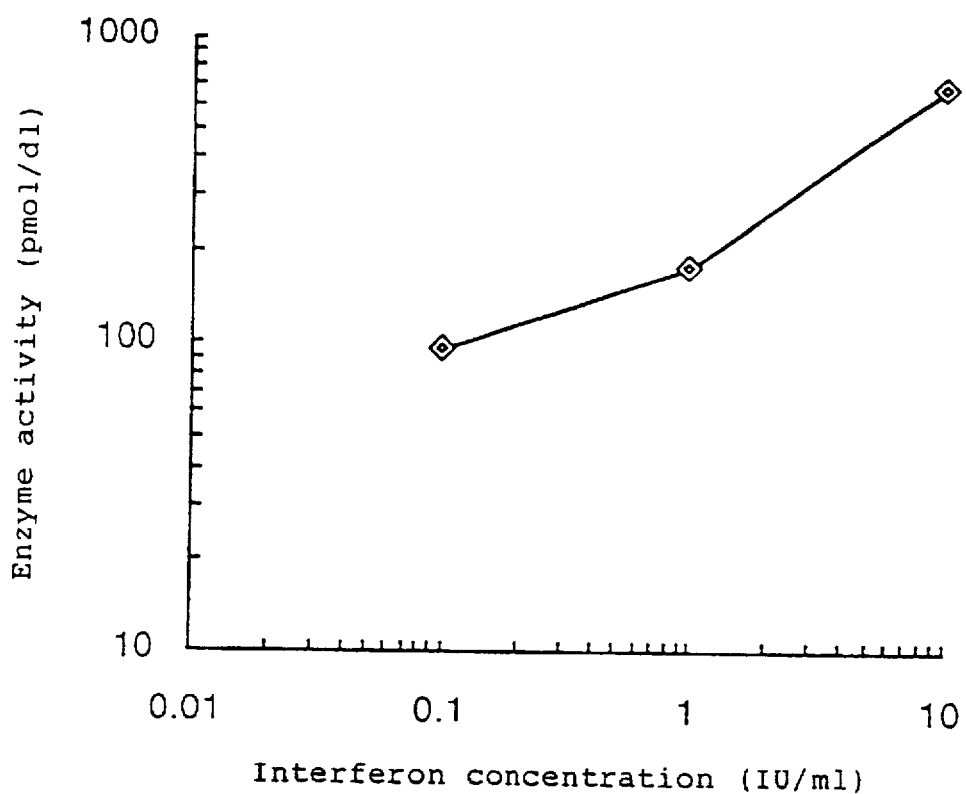
FIG. 7 is a graph showing the relationship between the concentration of interferon-α and the activity of 2'→5' oligoadenylate synthetase obtained in a manner similar to that described in FIG. 1 above except that cells used are human monocites (see, Example 7 below).

FIG. 7 shows that there is a relationship between the concentration of interferon-α and the activity of 2'→5' oligoadenylate synthetase. This means that it is possible to measure the activity of interferon-α using human monocyte too.

EXAMPLE 8

One hundred fifty microliters each of human serum, each containing interferon-α of different and known activity were placed in a 96-well cell culture plate separately as a sample. To the plate was added THP-1 cells ($6 \times 10^4$) suspended in 150 μl of RPMI1640 medium. After incubating for 20 hr at 37° C. under 5% $CO_2$ gas-phase, the cells were disrupted by freezing and thawing method. The activity of 2'→5' oligoadenylate synthetase in the resulting solution was determined in a manner similar to that of Example 1. The value obtained by subtracting the blank value from each measurement was plotted as enzyme activity in FIG. 8, wherein the ordinate shows the enzyme activity and the abscissa the concentration of interferon-α.

Figure 8:
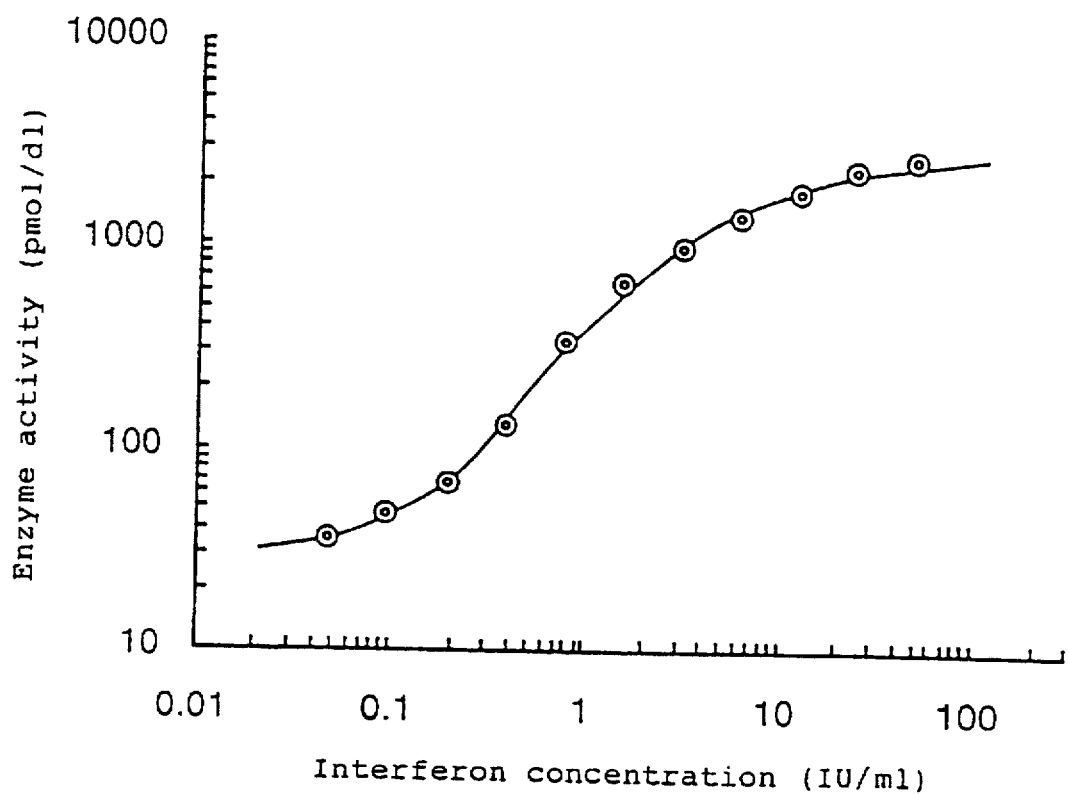
FIG. 8 is a graph showing the relationship between the concentration of interferon-α and the activity of 2'→5' oligoadenylate synthetase obtained in a manner similar to that described in FIG. 2 above except that 96- well cell culture plate was used instead of tube (see, Example 8 below).

FIG. 8 shows that a relationship between the concentration of interferon-α and the activity of 2'→5' oligoadenylate synthetase can be observed even when the measurement is carried out in smaller scale using 96-well cell culture plate compared to that in Example 1 where a tube is used. This means that the method of the present invention is also applicable to the measurement of interferon-α in 96-well cell culture plate.

EXAMPLE 9

One hundred fifty microliters each of human serum, each containing 50, 25, 12.5, 6.25, 3.13, 1.56, 0.781, 0.391, 0.196 or 0.098 IU/ml interferon-α, were placed in a 96-well cell culture plate. To the plate was added THP cells ($6 \times 10^4$) suspended in 200 μl of RPMI1640 medium. After incubating for 20 hr at 37° C. under 5% $CO_2$ gas-phase, the cells were disrupted by freezing and thawing method. The activity of 2'→5' oligoadenylate synthetase in the resulting solution was determined in a manner similar to that of Example 1. The concentration of interferon-α was evaluated from the resultant enzyme activity on the basis of calibration curve prepared in a manner similar to that described in Example 8. The results are shown in Table 1 below.

COMPARATIVE EXAMPLE 1

The interferon-α in the same samples used in Example 9 was determined by a bioassay (CPE method) using FL cell and Sindbis virus and a radioimmunoassay (RIA) using interferon-α RIA kit (Dainabot Co. Ltd., Tokyo, Japan). The results are shown in Table 1 below.

TABLE 1

| Concentration of added Interferon (IU/ml) | Example 9 (IU/ml) | Comparative example 1 (IU/ml) | |
|---|---|---|---|
| | | Bioassay method | RIA method |
| 0.098 | 0.08 | N.D. | N.D. |
| 0.196 | 0.14 | N.D. | N.D. |
| 0.391 | 0.34 | N.D. | N.D. |
| 0.781 | 0.90 | N.D. | N.D. |
| 1.56 | 1.87 | N.D. | N.D. |
| 3.13 | 4.74 | N.D. | N.D. |
| 6.25 | 6.97 | 11.7 | N.D. |
| 12.5 | 10.7 | 12.9 | 18.4 |
| 25.0 | 21.4 | 30.7 | 31.9 |
| 50.0 | 58.1 | 57.1 | 57.8 |

N.D.: not detected.

Table 1 shows that, according to the method of the present invention, interferon-α of lower concentration which is not detectable by conventional methods can be measured. It also shows that the concentration of interferon-α added to a sample is in good agreement with the calculated value obtained in Example 9, demonstrating that the method of the present invention is highly reliable.

The procedures used in Comparative Example 1 are as follows.

CPE method was carried out according to Yamazaki's method (S. Yamazaki, Pharma Medica, 4 (9): 111–118, 1986).

RIA method was conducted using the above-mentioned interferon-a RIA kit, which is a radioimmunoassay kit for sandwich method wherein sheep polyclonal antibody is used as first antibody and $^{125}I$ labeled mouse monoclonal antibody as second antibody. The procedures are shown in more detail below.

One hundred microliters of a sample or an authentic sample was placed in a polystyrene 54-well plate, one of accessories of the kit. To the authentic sample for serum was added 100 μl of normal serum, and to the rest of samples was added 100 μl of PBS containing 0.5% BSA. To each well was added an antibody bead (one of accessories of the kit) previously dampened with distilled water and the plate was incubated at 37° C. for 20±2 hr. After discarding the solution in wells, antibody beads in the wells were washed thrice with 250 μl of distilled water. Two hundred microliters of $^{125}I$ labeled anti-interferon antibody solution attached to the kit was added. After incubating for 3 hr at 37° C., the antibody solution was discarded. The bead was washed thrice with 250 µl of distilled water and the radioactivity absorbed onto antibody bead was measured on gamma counter. The result was used to evaluate the amount of interferon in a sample on the basis of calibration curve prepared using the results obtained by treating an authentic sample simultaneously in the same manner.

EXAMPLE 10

A patient suffering from hepatitis B was administered intramuscularly with a preparation containing interferon-α (a preparation containing recombinant human interferon-$\alpha_{2a}$, CANFERON, Takeda Chemical Industries, Ltd., Japan). After 3 and 6 hr from the administration, 150 µl of serum samples were obtained from the patient and placed in a 96-well cell culture plate. To the plate was added THP-1 cell (6×10) suspended in 150 pl of RPMI1640 medium. After incubating for 20 hr at 37° C. under 5% $CO_2$ gas-phase, the cells were disrupted by freezing and thawing method. The activity of 2'→5' oligoadenylate synthetase in the resulting solution was determined in a manner similar to that of Example 1. The concentration of interferon-α was evaluated from the resultant enzyme activity on the basis of calibration curve prepared in a manner similar to that described in Example 8. The results are shown in Table 2 below.

COMPARATIVE EXAMPLE 2

The interferon-α in the same samples used in Example 10 was determined by a bioassay (CPE method) using FL cell and Sindbis virus. The results are shown in Table 2 below.

TABLE 2

| Time after the administration (hr) | Example 10 (IU/ml) | Comparative example 2 (conventional method) (IU/ml) |
|---|---|---|
| 3 | 20.4 | 28.3 |
| 6 | 51.9 | 47.5 |

As is clear from Table 2, in the case of serum samples containing interferon-α at a concentration high enough to be measured by a conventional method such as CPE method, the measurements obtained by the present method is in good agreement with those obtained by the conventional method.

The results in Tables 1 and 2 indicate that it is possible to measure the activity of interferon in actual clinical samples according to the method of the present invention.

What is claimed is:

1. A method for measuring the amount of total interferon-alpha, beta, and omega in a sample comprising determining the activity of 2'-5'-adenylate synthetase induced in cells contacted by said sample wherein the improvement is using a cell line selected from the group consisting of THP-1, U-937, H9, FL, and WISH.

2. The method as recited in claim 1, wherein the cell line is selected from the group consisting of THP-1 and U-937.

* * * * *